US008114195B2

(12) United States Patent
Ni et al.

(10) Patent No.: US 8,114,195 B2
(45) Date of Patent: Feb. 14, 2012

(54) POROUS CRYSTALLINE MATERIALS, THEIR SYNTHESIS AND USE

(75) Inventors: Zheng Ni, Clinton, NJ (US); John Zengel, Clinton, NJ (US); David L. Stern, Asbury, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 405 days.

(21) Appl. No.: 12/455,732

(22) Filed: Jun. 5, 2009

(65) Prior Publication Data

US 2010/0307336 A1    Dec. 9, 2010

(51) Int. Cl.
*B01D 53/02* (2006.01)
*C01B 39/00* (2006.01)
(52) U.S. Cl. .............. 95/116; 95/128; 95/143; 548/101
(58) Field of Classification Search .................... 96/108; 95/116, 127, 128, 130, 138, 140, 141, 143, 95/900; 548/101; 502/400, 401; 423/210, 423/413
See application file for complete search history.

(56) References Cited

U.S. PATENT DOCUMENTS

| | | | |
|---|---|---|---|
| 2007/0202038 A1 | 8/2007 | Yaghi et al. | |
| 2009/0214407 A1* | 8/2009 | Reyes et al. | 423/230 |
| 2009/0216059 A1* | 8/2009 | Reyes et al. | 585/823 |
| 2010/0132549 A1* | 6/2010 | Yaghi et al. | 95/128 |
| 2010/0186588 A1* | 7/2010 | Yaghi et al. | 95/127 |

FOREIGN PATENT DOCUMENTS

JP           2007087737        4/2007

OTHER PUBLICATIONS

Bo Wang, et al., "Colossal cages in zeolitic imidazolate frameworks as selective carbon dioxide reservoirs", *Nature*, vol. 453, May 2008, pp. 207-211.
Lynda M. Nguyen, et al., "Convenient synthesis of copper (I) thiolates and related compounds", *Inorganica Chimica Acta*, 358, 2005, pp. 1331-1336.
Rahul Banerjee, et al., "High-throughput Synthesis of Zeolitic Imidazolate Frameworks and Application to CO2 Capture", *Science*, vol. 319, Feb. 2008, pp. 939-943.
Kyo Sung Park, et al, "Exceptional chemical and thermal stability of zeolitic imidazolate frameworks", *PNAS*, Jul. 2006, vol. 103, No. 27, pp. 10186-10191.
Hideki Hayashi, et al., "Zeolite A imidazolate frameworks", *Nature*, vol. 6, Jul. 2007, pp. 501-506.
William Morris, et al., "Crystals as Molecules : Postsynthesis Covalent Functionalization of Zeolitic Imidazolate Frameworks", *Journal of the American Chemical Society*, 2008, 130, pp. 12626-12627.

Barton H. Hamilton, et al., "Construction of a Functional Layered Solid Using the Tetrakis(imidazolyl)borate Coordinating Anion", *Inorganic Chemistry*, vol. 41, 2002, pp. 4984-4986.
Barton H. Hamilton, et al., "Lead and Thallium Tetrakis(imidazolyl)borates : Modifying Structure by Varying Metal and Anion", *Inorganic Chemistry*, vol. 43, 2004, pp. 4272-4277.
Lobbia G. G. Effendy, et al., "Synthesis, characterization and X-ray structural studies of novel dinuclear silver(I) complexes of poly(azolyl)borate ligands", *Inorganica Chimica Acta*, 308, 2000, pp. 65-72.
Nathan W. Ockwig, et al., "Reticular Chemistry: Occurrence and Taxonomy of Nets and Grammar for the Design of Frameworks", *Accounts of Chemical Research*, vol. 38, No. 3, 2005, pp. 176-192.
Sherman Chao, et al., "Studies in the Tetraarylborates Part VII. The Preparation and Reagent Properties of Some New Nitrogen Heterocyclic Tetraarylborates—Especially Sodium Tetrakis(1-Imidazolyl)borate, A Novel Gravimetric Reagent for Hydrogen Ion", *Analytica Chimica Acta*, 100, 1978, pp. 457-467.
Steven J. Rettig, et al., "Iron(II) 2-methylimidazolate and copper(II) 1,2,4-triazolate complexes: systems exhibiting long-range ferromagnetic ordering at low temperatures", *Can. J. Chem.*, 77, 1999, pp. 425-433.
Yun-Qi Tian, et al., "$[Co_5(im)_{10} \cdot 2MB]_\infty$: A Metall-Organic Open-Framework with Zeolite-Like Topology", *Angew. Chem. Int. Ed*, 2002, 41, pp. 1384-1386.
Yun-Qi Tian, et al., "The Silica-Like Extended Polymorphism of Cobalt (II) Imidazolate Three-Dimensional Frameworks: X-ray, Single-Crystal Structures and Magnetic Properties", *Chem. Eur. J.*, 2003, 9, pp. 5673-5685.
Xiao-Chun Huang, et al., "Ligand-Directed Strategy for Zeolite-Type Metal-Organic Frameworks : Zinc(II) Imidazolates with Unusual Zeolitic Topologies", *Angew. Chem. Int., Ed.*, 2006, 45, pp. 1557-1559.
Yun-Qi Tian, et al., "Design and Generation of Extended Zeolitic Metal-Organic Frameworks (ZMOFs) : Synthesis and Crystal Structures of Zinc(II) Imidazolate Polymers with Zeolitic Topologies", *Chem. Eur. J.*, 2007, 13, pp. 4146-4154.
Huang Xiaochun, et al., "[Zn(bim)2] • (H2O)1.67 : A metal-organic open-framework with sodalite topology", *Chinese Science Bulletin*, vol. 48, No. 15, 2003, pp. 1531-1534.
Edith M. Flanigen, et al., "Chapter 2 Zeolites and Molecular Sieves : An Historical Perspective", *Studies in Surface Science and Catalysis*, 2nd Ed., 2001, pp. 11-35.
Mark E. Davis, et al., "Ordered porous materials for emerging applications", *Nature*, vol. 417, Jun. 2002, pp. 813-821.
Stephen T. Wilson, "Phosphate-Based Molecular Sieves: New Structures, Synthetic Approaches, and Applications", *Introduction to Zeolite Science and Practice*, 3rd revised edition, 2007, pp. 105-135.

\* cited by examiner

*Primary Examiner* — Frank Lawrence, Jr.

(57) ABSTRACT

A porous crystalline material has a tetrahedral framework comprising a general structure, $M^1$-IM-$M^2$, wherein $M^1$ comprises a metal having a first valency, wherein $M^2$ comprises a metal having a second valency different from said first valency, and wherein IM is imidazolate or a substituted imidazolate linking moiety.

28 Claims, 3 Drawing Sheets

POROUS CRYSTALLINE MATERIALS, THEIR SYNTHESIS AND USE

FIELD

This invention relates to porous crystallline materials, their synthesis and their use.

BACKGROUND

One known family of porous crystallline materials are the zeolitic materials, which are based on the 3-dimensional, four-connected framework structure defined by corner-sharing [TO$_4$] tetrahedra, where T is any tetrahedrally coordinated cation. Among the known materials in this family are aluminosilicates that contain a three-dimensional microporous crystal framework structure of [SiO$_4$] and [AlO$_4$] corner sharing tetrahedral units, aluminophosphates that contain a three-dimensional microporous crystal framework structure of [AlO$_4$] and [PO$_4$] corner sharing tetrahedral units, and silicoaluminophosphates (SAPOs), in which the framework structure is composed of [SiO$_4$], [AlO$_4$] and [PO$_4$] corner sharing tetrahedral units. Included in the zeolitic family of materials are over 180 different porous framework types, many of which have great commercial value as catalysts and adsorbents.

Recently a new family of porous materials has been synthesized that is based on [M(IM)$_4$] tetrahedra in which IM is an imidazolate type linking moiety and M is a transition metal. These new materials are generally referred to as zeolitic imidazolate frameworks or ZIFs since the angle formed by imidazolates (IMs) when bridging transition metals is similar to the 145° angle of the Si—O—Si bond in zeolites. As a result, despite the infancy of this area of research, it has already been possible to synthesize ZIF counterparts of a large number of known zeolitic structures as well as produce porous framework types hitherto unknown to zeolites. Discussion of this research can be found in, for example, the following publications from Professor Yaghi and his co-workers: "Exceptional Chemical and Thermal Stability of Zeolitic Imadazolate Frameworks", *Proceedings of the National Academy of Sciences of U.S.A.*, Vol. 103, 2006, pages 10186-10191, "Zeolite A Imidazolate Frameworks", *Nature Materials*, Vol. 6, 2007, pages 501 to 506, "High-Throughput Synthesis of Zeolitic Imidazolate Frameworks and Application to CO$_2$ Capture", *Science*, Vol. 319, 2008, pages 939 to 943, "Colossal Cages in Zeolitic Imidazolate Frameworks as Selective Carbon Dioxide Reservoirs", *Nature*, Vol. 453, 2008, pages 207 to 212, and "Crystals as Molecules: Postsynthesis Covalent Functionalization of Zeolitic Imidazolate Frameworks", *Journal of the American Chemical Society*, Vol. 130, 2008, pages 12626 to 12627.

Much of this work on ZIF structures is summarized in U.S. Patent Application Publication No. 2007/0202038, the entire contents of which are incorporated herein by reference. In particular, the '038 application discloses a zeolitic framework, comprising the general structure: M-L-M, wherein M comprises a transition metal and L is a linking moiety comprising a structure selected from the group consisting of I, II, III, or any combination thereof:

wherein $A^1$, $A^2$, $A^3$, $A^4$, $A^5$, $A^6$, and $A^7$ can be either C or N, wherein $R^5$-$R^8$ are present when $A^1$ and $A^4$ comprise C, wherein $R^1$, $R^4$ or $R^9$ comprise a non-sterically hindering group that does not interfere with M, wherein $R^2$, $R^3$, $R^5$, $R^6$, $R^7$, $R^8$, $R^{10}$, $R^{11}$, and $R^{12}$ are each individually an alkyl, halo-, cyano-, nitro-, wherein $M^1$, $M^2$, $M^3$, $M^4$, $M^5$, and $M^6$ each comprise a transition metal, wherein when the linking moiety comprises structure III, $R^{10}$, $R^{11}$, and $R^{12}$ are each individually electron withdrawing groups. The '038 application also discloses that the zeolitic frameworks are useful as catalyst supports and as adsorbents for gases, particularly carbon dioxide.

In the zeolitic frameworks claimed in U.S. Patent Application Publication No. 2007/0202038, the metal species are all transition metals, typically tetrahedrally-coordinated divalent transition metals, especially $Zn^{2+}$ and $Co^{2+}$. The only example disclosed in U.S. Patent Application Publication No. 2007/0202038 that contains mixed-valence metals is ZIF-5, which has a non-porous framework comprising octahedrally-coordinated $In^{3+}$ in addition to tetrahedrally-coordinated $Zn^{2+}$.

In addition, a number of materials having framework structures comprising a metal cation and an anion which is either [B(IM)$_4$]$^-$ or [Al(IM)$_4$]$^-$ are known in the literature. However, most of these materials do not have a tetrahedral framework and/or appear to be non-porous structures.

For example, a cationic layered structure [PbB(IM)$_4$](NO$_3$) and its neutral iso-structure TlB(IM)$_4$ were reported by Ziegler et al. in 2002 and 2004, respectively. See Ziegler et al. "Construction of a Functional Layered Solid Using Tetrakis(imidazolyl)borate Coordinating Anion", *Inorganic Chemistry*, Vol. 41, 2002, pages 4984 to 4986 and Ziegler et al. "Lead and Thallium Tetrakis(imidazolyl)borates: Modifying Structure by Varying Metal and Anion", *Inorganic Chemistry*, Vol. 43, 2004, pages 4272 to 4277. However, although $Pb^{2+}$ and $Tl^+$ in the aforementioned structures assume a coordination number of four, their coordination geometries severely deviate from tetrahedral. As a result the products reported by Ziegler et al. appear to be generally two-dimensional layered structures as distinct from zeolitic or zeolite-like open frameworks.

A compound formulated AgB(IM)$_4$ was reported by Pettinari et al. in 2000 and a compound formulated CuB(IM)$_4$ was reported by Pike et al. in 2005. See Pettinari et al. "Synthesis, Characterization and X-ray Structural Studies of Novel Dinuclear Silver(I) Complexes of Poly(azolyl)borate Ligands", *Inorganic Chimica Acta*, Vol. 308, 2000, pages 65 to 72 and Pike et al. "Convenient Synthesis of Copper (I) Thiolates and Related Compounds", *Inorganic Chimica Acta*, Vol. 358, 2005, pages 1331 to 1336. The silver and copper compounds were synthesized in methanol and water, respectively. Although the aforementioned formula are consistent with tetrahedral frameoworks, no information about the crystal structure or crystallinity of these two materials was reported. More importantly, the aforementioned formula were assigned to the as-synthesized materials based on elemental analyses. The fact that the two materials in their as-synthesized form do not contain guest species, e.g. solvent molecules, within the frameworks is a strong evidence of the materials being non-porous.

JP Patent Application Publication No. 2007087737 "Lithium Ion Conducting Material and Secondary Lithium Ion Battery Using It" discloses a series of lithium salts formulated Li$^+$[M(Azo)$_{4-n}$(Q)$_n$]$^-$, wherein M is either B or Al, wherein Azo is an azole residue or a substituted azole residue, wherein Q is a residue of a compound except for azoles, and wherein n is 0, 1, 2, 3. The preparative method for the lithium salts with n=0 is exemplified in the synthesis of LiAl(IM)$_4$, wherein IM is imidazolate, and involves reacting LiAlH$_4$ with imidazole. Elemental analysis of the as-synthesized material was reported to be consistent with the formula LiAl(IM)$_4$. The fact that this material in the as-synthesized form does not contain guest species, e.g. solvent molecules, within the framework is a strong evidence of it being non-porous.

According to the present invention, a new series of porous crystalline materials has been synthesized which have a tetrahedral framework comprising a general structure, M$^1$-IM-M$^2$, wherein M$^1$ comprises a metal having a first valency and particularly a monovalent metal selected from Li$^+$, Cu$^+$, and Ag$^+$, wherein M$^2$ comprises a metal having a second valency different from said first valency and particularly a trivalent element selected from B$^{3+}$, Al$^{3+}$, and Ga$^{3+}$, and wherein IM is imidazolate or a substituted imidazolate linking moiety. Such materials offer new opportunities for catalytic applications since, for example, Cu$^+$, Ag$^+$, Al$^{3+}$ and Ga$^{3+}$ exhibit different chemical behaviour than the divalent transition metals typically used for ZIF synthesis. Moreover, by employing low atomic weight elements Li and B, rather than transition metals, it should be possible to produce adsorbents with improved gas uptake on a gravimetric basis.

SUMMARY

In one aspect, the invention resides in a porous crystalline material having a tetrahedral framework comprising a general structure, M$^1$-IM-M$^2$, wherein M$^1$ comprises a metal having a first valency, wherein M$^2$ comprises a metal having a second valency different from said first valency, and wherein IM is imidazolate or a substituted imidazolate linking moiety.

In one embodiment, M$^1$ comprises a monovalent metal and M$^2$ comprises a trivalent element.

Conveniently, M$^1$ is a monovalent metal cation selected from Li$^+$, Cu$^+$, and Ag$^+$, particularly Li$^+$.

Conveniently, M$^2$ is a trivalent element cation selected from B$^{3+}$, Al$^{3+}$, and Ga$^{3+}$, particularly B$^{3+}$.

Typically, the tetrahedral framework has a framework type selected from the group consisting of crb, dft, cag, sod, mer, rho, ana, lta, dia, zni, gme, lcs, frl, gis, poz and moz.

In a further aspect, the invention resides in a porous crystalline material having a tetrahedral framework comprising a structure selected from the group consisting of IV, V, VI, or any combination thereof:

(IV)

(V)

(VI)

wherein A$^1$, A$^2$, A$^3$, A$^4$, A$^5$, A$^6$, and A$^7$ can be either C or N, wherein R$^5$-R$^8$ are present when A$^1$ to A$^4$ comprise C, wherein R$^1$, R$^4$ or R$^9$ comprise a non-sterically hindering group that does not interfere with the adjacent M$^1$ or M$^2$, wherein R$^2$, R$^3$, R$^5$, R$^6$, R$^7$, and R$^8$ are each individually hydrogen, alkyl, halo, cyano, or nitro, wherein M$^1$ comprises a monovalent metal cation, wherein M$^2$ comprises a trivalent element cation, and wherein R$^{10}$, R$^{11}$, and R$^{12}$ are each individually electron withdrawing groups.

In one embodiment, M$^1$ is Li$^+$, M$^2$ is B$^{3+}$, IM is IV, each of R$^1$, R$^2$ and R$^3$ is hydrogen, the tetrahedral framework has the cag framework type, and the as-synthesized material contains guest species within the tetrahedral framework.

In yet a further aspect, the invention resides in a method of adsorbing a gas comprising contacting the gas with the porous crystalline material described herein.

DETAILED DESCRIPTION OF THE EMBODIMENTS

Disclosed herein is a new family of porous crystalline materials having a tetrahedral framework comprising a general structure, $M^1$-IM-$M^2$, wherein $M^1$ comprises a metal having a first valency, wherein $M^2$ comprises a metal having a second valency different from said first valency, and wherein IM is imidazolate or a substituted imidazolate linking moiety. Also disclosed herein is a process for synthesizing the new family of materials and a method of using the materials to adsorb gases, such as carbon dioxide.

Typically, $M^1$, is a monovalent metal cation, such as $Li^+$, $Na^+$, $K^+$, $Cs^+$, $Rb^+$, $Cu^+$, $Ag^+$ and $Au^+$. More particularly, $M^1$ is a monovalent metal cation selected from $Li^+$, $Cu^+$, and $Ag^+$, particularly $Li^+$.

Typically, $M^2$ is a trivalent element cation, such as $B^{3+}$, $Al^{3+}$, $Ga^{3+}$, $In^{3+}$, $Fe^{3+}$, $Cr^{3+}$, $Sc^{3+}$, $Y^{3+}$, and $La^{3+}$ wherein La is any lanthanide metal. More particularly, $M^1$ is a trivalent element cation selected from $B^{3+}$, $Al^{3+}$, or $Ga^{3+}$, particularly $B^{3+}$.

Generally, the porous crystalline materials described herein have a tetrahedral framework comprising a structure selected from the group consisting of IV, V, VI, or any combination thereof:

wherein $A^1$, $A^2$, $A^3$, $A^4$, $A^5$, $A^6$, and $A^7$ can be either C or N, wherein $R^5$-$R^8$ are present when their respective $A^1$ to $A^4$ comprise C, wherein $R^1$, $R^4$ or $R^9$ comprise a non-sterically hindering group that does not interfere with the adjacent $M^1$ or $M^2$, wherein $R^2$, $R^3$, $R^5$, $R^6$, $R^7$, and $R^8$ are each individually hydrogen, alkyl, halo, cyano, or nitro, wherein $M^1$ comprises a monovalent metal cation, and wherein $M^2$ comprises a trivalent element cation, and wherein, if present, $R^{10}$, $R^{11}$, and $R^{12}$ are each individually electron withdrawing groups.

In one embodiment, each of $R^1$, $R^4$ and $R^9$ is independently selected from hydrogen, methyl, ethyl, nitro, formyl, halo, and cyano groups.

Suitable electron withdrawing groups for each of $R^{10}$, $R^{11}$, and $R^{12}$ include nitro, cyano, fluoro and chloro groups.

Examples of family members of the novel porous crystalline materials described herein comprise structures selected from the group consisting of VII, VIII, IX, X, XI, XII, XIII, XIV, XV, XVI, XVII, and XVIII:

(XVI)

(XVII)

(XVIII)

These imidazolate linking moieties have also been successfully used in the syntheses of ZIFs, as reported by Professor Yaghi and his co-workers in the following publications: "Exceptional Chemical and Thermal Stability of Zeolitic Imadazolate Frameworks", *Proceedings of the National Academy of Sciences of U.S.A.*, Vol. 103, 2006, pages 10186-10191, "Zeolite A Imidazolate Frameworks", *Nature Materials*, Vol. 6, 2007, pages 501 to 506, "High-Throughput Synthesis of Zeolitic Imidazolate Frameworks and Application to $CO_2$ Capture", *Science*, Vol. 319, 2008, pages 939 to 943, "Colossal Cages in Zeolitic Imidazolate Frameworks as Selective Carbon Dioxide Reservoirs", *Nature*, Vol. 453, 2008, pages 207 to 212, and "Crystals as Molecules: Postsynthesis Covalent Functionalization of Zeolitic Imidazolate Frameworks", *Journal of the American Chemical Society*, Vol. 130, 2008, pages 12626 to 12627.

The new family of porous crystalline materials disclosed herein can have tetrahedral framework structures of any type. The framework type of a porous crystalline material is denoted herein by a mnemonic code consisting of three boldface lower-case letters. This system of symbols was introduced by Professors O'Keeffe and Yaghi, and adopted in the research on ZIFs. General information about the symbol system can be found, for example, in the publication by O'Keeffe and Yaghi et al. "Reticular Chemistry: Ocurrence and Taxonomy of Nets and Grammar for the Design of Frameworks", *Accounts of Chemical Research*, Vol. 38, 2005, pages 176 to 182, and at the Reticular Chemistry Structure Resource (RCSR) website http://rcsr.anu.edu.au/home. We note that the concepts "framework type", "topology" and "net" are used essentially interchangeably in the chemical literature. These mnemonic codes should not be confused or equated with actual materials.

Typically, a porous crystalline material of the present invention is iso-structural to a known ZIF, and assumes a tetrahedral framework type selected from the group consisting of crb, dft, cag, sod, mer, rho, ana, lta, dia, zni, gme, lcs, frl, gis, poz and moz. All of these framework types have been realized in the syntheses of ZIFs.

In one embodiment, the monovalent metal, $M^1$, is $Li^+$, the trivalent element, $M^2$, is $B^{3+}$, IM is imidazolate linking moiety, i.e. structure VII, and the tetrahedral framework has the cag framework type. The as-synthesized material contains guest species within the framework.

Synthesis of the present porous crystalline material is based on a reaction of $[M^1(L)_n]X_x$ and $A_a[M^2(IM)_4]$, wherein $M^1$, $M^2$ and IM are the same as described above, L is a neutral ligand, typically ammonia, an amine, phosphine, nitrile, or ether;

n is a non-negative integer ranging from 0 to 12;

X is an anion, typically a halide, nitrate, perchlorate, acetate, trifluoromethanesulfonate, or acetylacetonate;

A is a cation, typically $Na^+$, $K^+$, tetraalkylammonium $[NR_4]^+$, or tetraalkylphosponium $[PR_4]^+$; and x and a are each a non-negative integer.

The reaction takes place in a polar aprotic solvent and, in some cases, in the presence of a template. The polar aprotic organic solvent is typically an amide (e.g. N,N-dimethylformamide, N,N-dimethylacetamide, 1,3-dimethylpropyleneurea), a sulfoxide (e.g. dimethylsulfoxide), or a phosphoramide (e.g. hexamethylphosphoramide). If present, the template is typically a neutral organic compound, such as an ether, ketone, ester, amine, nitrile, nitro compound, phosphine, hydrocarbon, or halide.

Typically the synthesis procedure involves mixing a solution of $[M^1(L)_n]X_x$ and a solution of $A_a[M^2(IM)_4]$, both in a polar aprotic organic solvent, at a temperature of about $-78°$ C. (dry-ice bath temperature) to about $153°$ C. (the normal boiling point of N,N-dimethylformamide), and allowing the materials to react at this temperature for about 0.5 hour to about 72 hours. The molar ratio of $[M^1(L)_n]X_x$ to $A_a[M^2(IM)_4]$ is in the range from about 0.1 to about 10. If the by-product AX precipitates, the solid and the solution are separated. Optionally, a template compound is added to the solution at this point. The quantity of the template compound is in such a range that, at the lower limit, it is equimolar to one of the two reactants that is smaller in molar quantity, and at the upper limit, it is equimolar to the solvent. The solution is kept at a temperature of about $-78°$ C. to about $153°$ C. to allow the product to crystallize. When the crystallization step is completed, normally in about 0.5 hour to about 168 hours, the resultant porous crystalline material is recovered.

$Li^+$, $Cu^+$, $Ag^+$ are particularly effective in displacing the cation A ($Na^+$, $K^+$, $NR_4^+$, $PR_4^+$) of the reactant $A_a[M^2(IM)_4]$ because they all form significantly stronger bonds with the IM linking moiety than A. $Li^+$, $Cu^+$, $Ag^+$ are all effective in the crystallization of the present porous crystalline materials because they all prefer tetrahedral coordination.

The reactants $A_a[M^2(IM)_4]$ used in the syntheses of the present porous crystalline materials are prepared beforehand. The preparation is particularly convenient when $M^2=B^{3+}$, $Al^{3+}$, $Ga^{3+}$. The preparative procedures for the boron compound can be found in, for example, Moore et al. "Studies In The Tetraarylborates, Part VII. The Preparation and Reagent Properties of Some New Nitrogen Heterocyclic Tetraarylborates—Especially Sodium Tetrakis(1-Imidazolyl)borate, A Novel Gravimetric Reagent for Hydrogen Ion", *Analytica Chimica Acta*, Vol. 100, 1978, pages 457 to 467, and Ziegler et al. "Lead and Thallium Tetrakis(imidazolyl)borates: Modifying Structure by Varying Metal and Anion", *Inorganic Chemistry*, Vol. 43, 2004, pages 4272 to 4277. These preparations all involve a reaction between $BH_4^-$ and H-IM, wherein H-IM is imidazole or a substituted imidazole. This chemistry is applicable to $Al^{3+}$ and $Ga^{3+}$ because Al and Ga exhibit chemical properties similar to B and because the $AlH_4^-$ and $GaH_4^-$ compounds are readily available.

The present porous crystalline materials in the as-synthesized form contain guest species, typically solvent and/or template molecules, within the tetrahedral frameworks. The guest species can be removed either by evacuation at a pressure less than 50 mTorr at a temperature of about 70° C. to about 300° C., or by exchange with an organic solvent of small molecular size, e.g. acetonitrile, followed by the evacuation process described above. The removal of guest species results in internal pore volume that can be used to adsorb various gases, such as carbon dioxide, carbon monoxide, hydrocarbons, hydrogen, nitrogen, oxygen, noble gases and amines.

The size and shape of the pores in the present crystalline materials can be controlled by the choice of imidazolate linking moiety, solvent and template. As a result, the present porous crystalline materials show significant potential for use as catalysts and in the storage and separation of gases.

From the viewpoint of catalysis, the incorporation of $Cu^+$, $Ag^+$, $Al^{3+}$, and $Ga^{3+}$ will enable unique catalytic chemistry that is unavailable to the metals used thus far for ZIFs, typically divalent transition metals, such as $Zn^{2+}$, $Co^{2+}$.

In the area of gas storage and separation, which is currently the most important application of ZIFs, the use of very light metals, such as Li and B, is highly desirable for improving gas uptake on a gravimetric basis. For example, a porous material with chemical composition $LiB(IM)_4$ is expected to show 39% higher uptake in the unit of mmole/g than the iso-structural $Zn(IM)_2$ material (the formula weights of $Li_{0.5}B_{0.5}(IM)_2$ and $Zn(IM)_2$ are 143 and 199, respectively; here IM is imidazolate).

The invention will now be more particularly described with reference to the Examples and the accompanying drawings.

EXAMPLE 1

A solution of 14 mg lithium chloride (LiCl, 0.33 mmole) in 5 mL N,N-dimethylformamide (DMF) was added to a solution of 100 mg sodium tetrakis(1-imidazolyl)borate (NaB(IM)$_4$, 0.33 mmole) in 5 mL DMF in a 20-mL glass vial. When the precipitation of sodium chloride completed (typically in about 2 hrs), the clear solution was transferred to another 20-mL glass vial, and mixed with 5 mL tetrahydrofuran (THF). Polyhedral crystals appeared shortly on the glass wall and were allowed to grow over a period of about 8 hrs. The mother liquor was then removed and the crystals were washed thoroughly with THF and dried in vacuo. 35 mg of highly crystalline product LiB(IM)$_4$.Guest (Compound 1) was obtained (30% yield; Guest is a mixture of THF and DMF).

A colorless polyhedron-shaped crystal of Compound 1 with approximate dimensions 0.08×0.19×0.21 mm, was used for X-ray crystallographic analysis. The X-ray intensity data were measured at 133(2) K, cooled by Rigaku-MSC X-Stream 2000, on a Bruker SMART APEX CCD area detector system equipped with a graphite monochromator and a MoKα fine-focus sealed tube (α=0.71073 Å) operated at 1600 watts power (50 kV, 32 mA). The detector was placed at a distance of 5.8 cm from the crystal.

A total of 1515 frames were collected with a scan width of 0.3° in ω and an exposure time of 20 seconds/frame. The total data collection time was about 11 hours. The frames were integrated with the Bruker SAINT software package using a narrow-frame integration algorithm. The integration of the data using a Orthorhombic unit cell yielded a total of 27071 reflections to a maximum θ angle of 28.40° (0.90 Å resolution), of which 4692 were independent, completeness=98.3%, $R_{int}$=0.0759, $R_{sig}$=0.0611 and 3273 were greater than 2σ (I). The final cell constants: a=14.382(5) Å, b=14.809(5) Å, c=17.869(6) Å, α=90°, β=90°, γ=90°, volume=3806(2) Å$^3$, were based upon the refinement of the XYZ-centroids of 2336 reflections above 20σ (I) with 2.278°<θ<23.570°. Analysis of the data showed negligible decay during data collection. Data were corrected for absorption effects using the multi-scan technique (SADABS). The ratio of minimum to maximum apparent transmission was 0.5697.

The structure was solved and refined using the Bruker SHELXTL (Version 6.1) Software Package, using the space group Pbca with Z=8 for the formula unit Li B C16 H20 N8 O, i.e., LiB(IM)$_4$.THF. The five non-hydrogen atoms of the THF molecule were clearly revealed in difference Fourier maps. However, refinement of these atoms was unsuccessful due to a slight disorder of the THF molecule that was not easy to model accurately. The disorder was caused by the superimposition of THF and DMF, which were respectively the major and minor components of the guest mixture. In order to improve the refinement of the light atoms on the framework, PLATON/SQUEEZE routine was used to remove the electron density of the disordered guest molecules. Final anisotropic full-matrix least-squares refinement on F$^2$ with 199 variables converged at R1=7.24% for the observed data and wR2=17.77% for all data. The goodness-of-fit was 1.041. The largest peak on the final difference map was 0.289 e$^-$/Å$^3$ and the largest hole was −0.267 e$^-$/Å$^3$. Based on the final model, the calculated density of the crystal is 0.998 g/cm$^3$ and F(000) amounts to 1184 electrons.

The validity of this structure is supported by the R factors, goodness-of-fit and residual electron densities described above and by very reasonable displacement parameters of the framework atoms listed in Table 1. In addition, the treatment of the guest portion of the structure is validated by the results of PLATON/SQUEEZE shown in Table 2. The routine has identified eight cavities per unit cell. Each has a volume of 146 to 148 Å$^3$ and contains 38 electrons. Both the volume and the electron count support the assignment of one guest molecule per cavity (both THF and DMF have 5 non-hydrogen atoms and 40 electrons per molecule), and therefore the formula of the crystal LiB(IM)$_4$.Guest.

TABLE 1

Atomic coordinates and equivalent isotropic atomic displacement parameters (Å$^2$) for Compound 1
U(eq) is defined as one third of the trace of the orthogonalized $U_{ij}$ tensor.

|     | x           | y            | z           | U(eq)      |
| --- | ----------- | ------------ | ----------- | ---------- |
| N1  | 0.91688(12) | 0.16097(12)  | 0.62417(9)  | 0.0176(4)  |
| N4  | 1.14471(13) | −0.01735(13) | 0.64484(11) | 0.0277(5)  |
| N7  | 0.95613(12) | 0.19942(12)  | 0.75802(9)  | 0.0182(4)  |
| N5  | 1.05049(11) | 0.26554(12)  | 0.64962(9)  | 0.0172(4)  |
| N2  | 0.84096(13) | 0.13435(14)  | 0.51725(10) | 0.0256(4)  |
| N3  | 1.06254(12) | 0.10166(12)  | 0.68310(9)  | 0.0173(4)  |
| N6  | 1.17178(13) | 0.35073(13)  | 0.61547(11) | 0.0239(4)  |
| N8  | 0.88028(13) | 0.26633(14)  | 0.85190(10) | 0.0259(4)  |
| C9  | 1.14427(14) | 0.27288(15)  | 0.64364(12) | 0.0208(5)  |
| C6  | 1.07483(15) | 0.03737(15)  | 0.63057(12) | 0.0218(5)  |
| C12 | 0.92037(15) | 0.27681(15)  | 0.78558(12) | 0.0223(5)  |
| B1  | 0.99664(16) | 0.18318(16)  | 0.67886(13) | 0.0173(5)  |
| C7  | 1.01622(16) | 0.34659(15)  | 0.62324(13) | 0.0234(5)  |
| C3  | 0.91335(15) | 0.17280(15)  | 0.54931(12) | 0.0217(5)  |
| C10 | 0.93655(17) | 0.13448(16)  | 0.81107(13) | 0.0282(5)  |
| C8  | 1.09050(16) | 0.39694(16)  | 0.60277(13) | 0.0256(5)  |
| C1  | 0.83986(17) | 0.10941(18)  | 0.64045(14) | 0.0335(6)  |
| C2  | 0.79516(18) | 0.0938(2)    | 0.57474(14) | 0.0368(6)  |
| C5  | 1.18061(16) | 0.01327(16)  | 0.71150(14) | 0.0287(5)  |
| C11 | 0.89095(17) | 0.17620(16)  | 0.86780(13) | 0.0299(6)  |
| C4  | 1.13132(16) | 0.08573(15)  | 0.73551(13) | 0.0247(5)  |
| Li1 | 0.8107(3)   | 0.1311(2)    | 0.4063(2)   | 0.0207(8)  |

TABLE 2

Location and volume of and number of electrons within the cavities in the unit cell of Compound 1

| Cavity | Coordinates of Centroid | | | Volume ($Å^3$) | Electron ($e^-$) |
| --- | --- | --- | --- | --- | --- |
| | X | Y | Z | | |
| 1 | 0.341 | 0.305 | 0.401 | 147 | 38 |
| 2 | 0.841 | 0.305 | 0.099 | 147 | 38 |
| 3 | 0.341 | 0.194 | 0.901 | 148 | 38 |
| 4 | 0.841 | 0.194 | 0.599 | 148 | 38 |
| 5 | 0.159 | 0.805 | 0.401 | 146 | 38 |
| 6 | 0.659 | 0.805 | 0.099 | 146 | 38 |
| 7 | 0.159 | 0.694 | 0.901 | 146 | 38 |
| 8 | 0.659 | 0.694 | 0.599 | 146 | 38 |

Figure 1:
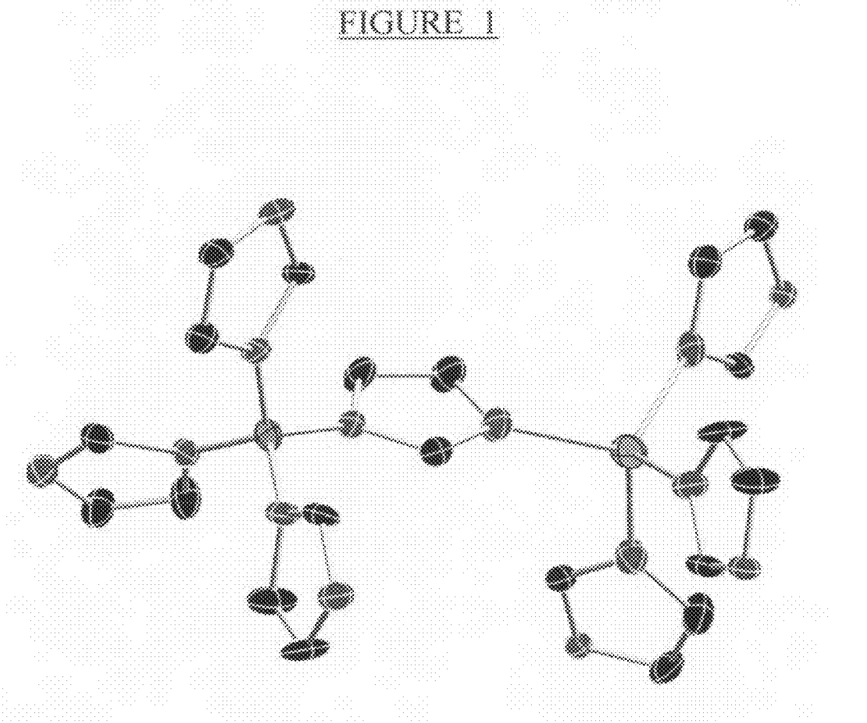
FIG. 1 is an Oak Ridge Thermal Ellipsoid Plot (ORTEP) of Compound 1 of Example 1.

Compound 1 has a tetrahedral framework of mixed-valence metal imidazolate, $M^1M^2(IM)_4$, wherein $M^1$ and $M^2$ are monovalent and trivalent element cations, respectively. This is clearly depicted in an Oak Ridge Thermal Ellipsoid Plot (ORTEP) of Compound 1, showing two adjacent metal cations, $Li^+$ and $B^{3+}$, both tetrahedrally coordinated by four imidazolate linkers (FIG. 1). The lengths of Li—N and B—N bonds all fall in the ranges well established in the literature (Table 3), confirming the correct assignment of the identity of the metals. The tetrahedral coordination geometry of each metal cation is near perfect, evidenced by N—Li—N and N—B—N bond angles, all of which are very close to the ideal tetrahedral angle of 109.5° (Table 3). For comparison, Table 3 also lists N—Tl—N and N—B—N bond angles observed in the single-crystal structure of the two-dimensional layered compound $TlB(IM)_4$ disclosed by Ziegler et al. in "Lead and Thallium Tetrakis(imidazolyl)borates: Modifying Structure by Varying Metal and Anion", *Inorganic Chemistry*, Vol. 43, 2004, pages 4272 to 4277. The non-tetrahedral coordination of $Tl^+$ discourages the formation of zeolitic or zeolite-like open frameworks, whereas the tetrahedral coordination of $Li^+$ facilitates such.

TABLE 3

Bond lengths and angles involving $Li^+$ or $B^{3+}$ observed in the crystal structure of Compound 1 and bond angles involving $Tl^+$ or $B^{3+}$ observed in the crystal structure of the layered compound $TlB(IM)_4$

| Bond lengths of Compound 1 (Å) | | Bond angles of Compound 1 (°) | | Bond angles of $TlB(IM)_4$ (°) | |
| --- | --- | --- | --- | --- | --- |
| Li—N | B—N | N—Li—N | N—B—N | N—Tl—N | N—B—N |
| 2.021 | 1.536 | 104.289 | 108.000 | 77.093 | 107.774 |
| 2.030 | 1.537 | 106.639 | 108.808 | 78.757 | 107.824 |
| 2.053 | 1.542 | 109.412 | 109.191 | 78.899 | 109.180 |
| 2.062 | 1.549 | 109.802 | 109.240 | 89.721 | 110.183 |
| | | 112.985 | 109.393 | 92.251 | 110.381 |
| | | 113.159 | 112.148 | 155.030 | 111.501 |

Figure 2:
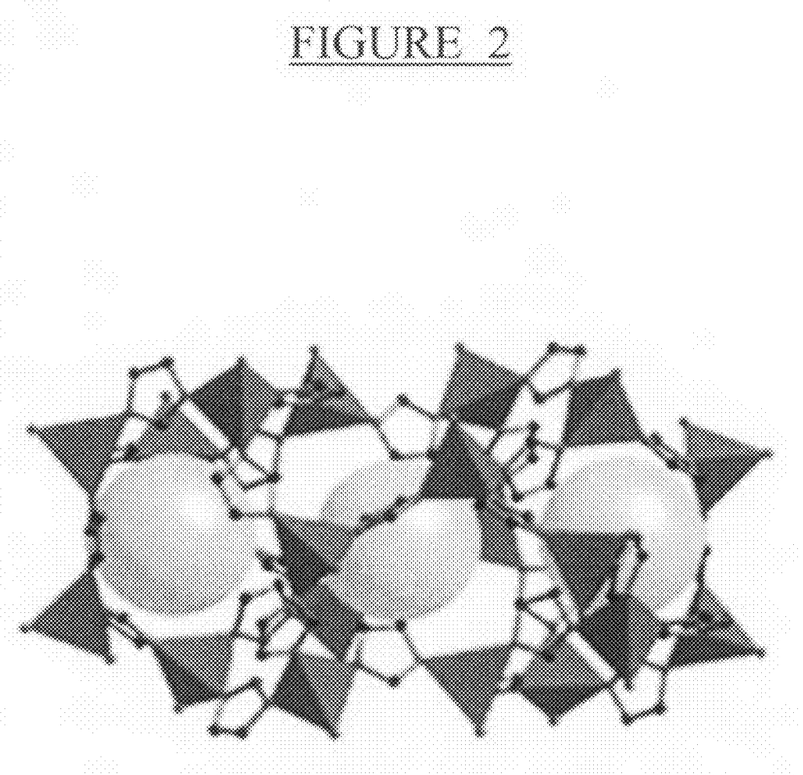
FIG. 2 illustrates the framework structure of ZIF-4 having the cag framework type.

The framework type of Compound 1 is the same as ZIF-4, which in turn is the same as that of mineral Calcium Gallate (denoted cag hereafter). Although the cag framework type is not a zeolitic framework type, it is a three-dimensional tetrahedral framework, and when adopted by a ZIF, it imparts the material internal cavities and 6-ring channels that can be accessible (FIG. 2). Table 4 compares the unit cell parameters of Compound 1 with those of ZIF-4 reported by Yaghi et al. in "Exceptional Chemical and Thermal Stability of Zeolitic Imadazolate Frameworks", *Proceedings of the National Academy of Sciences of U.S.A.*, Vol. 103, 2006, pages 10186-10191. They are identical except the slight contraction of Compound 1 in cell edges, which is expected based on typical bond lengths of Li—N, B—N and Zn—N. Therefore, the synthesis of Compound 1 demonstrates the concept of substituting divalent metal in a neutral tetrahedral framework of ZIF with alternating monovalent and trivalent elements while preserving the framework type.

TABLE 4

Comparison of the compositions and unit cell parameters of Compound 1 and ZIF-4.

| Material | Framework composition | Space group | Unit cell parameters | | |
| --- | --- | --- | --- | --- | --- |
| | | | a (Å) | b (Å) | c (Å) |
| ZIF-4 | $Zn(IM)_2$ | Pbca, orthorhombic | 15.395 (2) | 15.307 (2) | 18.426 (2) |
| Compound 1 | $LiB(IM)_4$ | Pbca, orthorhombic | 14.382 (5) | 14.809 (5) | 17.869 (6) |

EXAMPLE 2

Figure 3:
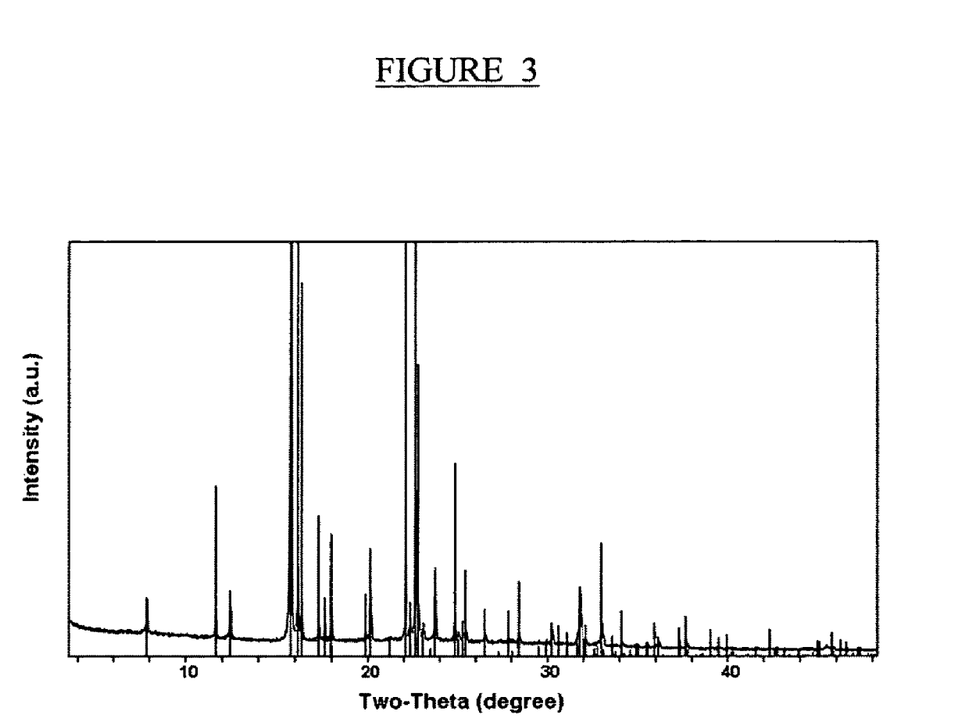
FIG. 3 is an overlay of the powder X-ray diffraction pattern of the needle-shaped microcrystalline Compound 2 of Example 2, shown as a continuous trace, and the pattern calculated from the structure of the large crystals of Compound 2 of Example 2, shown as a stick pattern.

To demonstrate the templating effect of THF in the synthesis of Compound 1, Example 1 was repeated without the addition of THF and produced a needle-shaped microcrystalline product $LiB(IM)_4$ (Compound 2). Large crystals of Compound 2 suitable for single-crystal X-ray diffraction were obtained from an alternative route, which is a very slow transformation from Compound 1 to Compound 2 in THF under ambient conditions. The crystal transformation process likely involves trace amount of water present in THF, and typically occurs to an appreciable extent in about one month. The needle-shaped microcrystalline product and the large crystals are the same crystalline phase, evidenced by the excellent agreement of the powder X-ray diffraction pattern of the former and the pattern calculated from the crystal structure of the latter (FIG. 3).

The crystal structure of Compound 2 was successfully solved and refined (Tables 5 and 6). The $LiB(IM)_4$ tetrahedral framework of Compound 2 is non-porous, and consequently does not contain guest species. This is evidenced by the very low residual electron densities of the final converged refinement of a structural model without any guest species (Table 5). The observed bond lengths are consistent with the typical values for Li—N and B—N bonds, and the observed bond angles confirm the tetrahedral coordination geometry of each T atom (Table 7). As far as framework type is concerned, Compound 2 is the mixed-valence counterpart of ZIF-61 with the zni framework type reported by Yaghi et al. in "High-Throughput Synthesis of Zeolitic Imidazolate Frameworks and Application to $CO_2$ Capture", *Science*, Vol. 319, 2008, pages 939 to 943 (Table 8). In comparison to ZIF-61, Compound 2 shows a slight contraction in cell edges due to the difference in bond lengths (Zn—N versus Li—N and B—N) and a slight lowering in space-group symmetry due to the replacement of the only unique T site ($Zn^{2+}$) with two alternating T sites ($Li^+$ and $B^{3+}$).

TABLE 5

Crystal data and structure refinement for Compound 2

| | |
| --- | --- |
| Empirical formula | C12H12BLiN8 [i.e., $LiB(IM)_4$] |
| Formula weight | 286.05 |
| Temperature | 100(2) K |
| Wavelength | 0.71073 Å |
| Crystal system, space group | Tetragonal, $I4_1cd$ |

TABLE 5-continued

Crystal data and structure refinement for Compound 2

| | |
|---|---|
| Unit cell dimensions | a = 22.4981(7) Å  α = 90° |
| | b = 22.4981(7) Å  β = 90° |
| | c = 11.5015(6) Å  γ = 90° |
| Volume | 5821.7(4) Å$^3$ |
| Z, Calculated density | 16, 1.305 g/cm$^3$ |
| Absorption coefficient | 0.086 mm$^{-1}$ |
| F(000) | 2368 |
| Crystal size | 0.13 × 0.02 × 0.02 mm |
| Theta range for data collection | 1.81° to 28.28°. |
| Limiting indices | −29 ≦ h ≦ 29, −29 ≦ k ≦ 29, |
| | −14 ≦ l ≦ 14 |
| Reflections collected/unique | 80347/3505 [R(int) = 0.1380] |
| Completeness to theta = 28.28 | 98.3% |
| Refinement method | Full-matrix least-squares on F$^2$ |
| Data/restraints/parameters | 3505/1/199 |
| Goodness-of-fit on F$^2$ | 0.969 |
| Final R indices [I > 2σ(I)] | R1 = 0.0345, wR2 = 0.0766 |
| R indices (all data) | R1 = 0.0493, wR2 = 0.0827 |
| Largest diff. peak and hole | 0.204 and −0.200 e-/Å$^3$ |

TABLE 6

Atomic coordinates (×10$^4$) and equivalent isotropic displacement parameters (Å$^2$ × 10$^3$) for Compound 2
U(eq) is defined as one third of the trace of the orthogonalized Uij tensor.

| | x | y | z | U(eq) |
|---|---|---|---|---|
| B(1) | 1485(1) | 983(1) | 3244(1) | 12(1) |
| C(1) | 2494(1) | 918(1) | 4386(1) | 15(1) |
| C(2) | 1958(1) | 1701(1) | 4775(1) | 16(1) |
| C(3) | 2471(1) | 1719(1) | 5396(1) | 16(1) |
| C(4) | 1396(1) | 1130(1) | 999(1) | 15(1) |
| C(5) | 1606(1) | 1940(1) | 1959(2) | 18(1) |
| C(6) | 1510(1) | 2068(1) | 817(1) | 20(1) |
| C(7) | 374(1) | 1311(1) | 3253(1) | 16(1) |
| C(8) | 694(1) | 973(1) | 4918(1) | 19(1) |
| C(9) | 100(1) | 1091(1) | 4981(1) | 22(1) |
| C(10) | 1162(1) | −128(1) | 3285(1) | 15(1) |
| C(11) | 1970(1) | 37(1) | 2293(1) | 16(1) |
| C(12) | 1826(1) | −549(1) | 2240(1) | 18(1) |
| Li(1) | 3556(1) | 1000(1) | 6061(2) | 16(1) |
| N(1) | 1969(1) | 1185(1) | 4119(1) | 13(1) |
| N(2) | 2812(1) | 1221(1) | 5154(1) | 16(1) |
| N(3) | 1534(1) | 1331(1) | 2087(1) | 13(1) |
| N(4) | 1375(1) | 1555(1) | 210(1) | 17(1) |
| N(5) | 873(1) | 1113(1) | 3800(1) | 13(1) |
| N(6) | −104(1) | 1308(1) | 3929(1) | 20(1) |
| N(7) | 1540(1) | 314(1) | 2969(1) | 13(1) |
| N(8) | 1315(1) | −656(1) | 2876(1) | 18(1) |

TABLE 7

Bond lengths and angles involving Li$^+$ or B$^{3+}$ observed in the crystal structure of Compound 2

| Bond lengths of Compound 2 (Å) | | Bond angles of Compound 2 (°) | |
|---|---|---|---|
| Li—N | B—N | N—Li—N | N—B—N |
| 2.034 | 1.544 | 102.948 | 107.606 |
| 2.065 | 1.547 | 105.536 | 108.089 |
| 2.083 | 1.547 | 106.496 | 108.896 |
| 2.091 | 1.551 | 108.060 | 109.950 |
| | | 115.254 | 111.123 |
| | | 117.511 | 111.156 |

TABLE 8

Comparison of the compositions and unit cell parameters of Compound 2 and ZIF-61

| | | | Unit cell parameters | | |
|---|---|---|---|---|---|
| Material | Framework composition | Space group | a (Å) | b (Å) | c (Å) |
| ZIF-61 | Zn(IM)$_2$ | I4$_1$/acd, Tetragonal | 23.4803 (3) | 23.4803 (3) | 12.5545 (3) |
| Compound 2 | LiB(IM)$_4$ | I4$_1$cd, Tetragonal | 22.4981 (7) | 22.4981 (7) | 11.5015 (6) |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A porous crystalline material having a tetrahedral framework comprising a general structure, M$^1$-IM-M$^2$, wherein M$^1$ comprises a metal having a first valency, wherein M$^2$ comprises a metal having a second valency different from said first valency, and wherein IM is imidazolate or a substituted imidazolate linking moiety, and wherein one or more of the following is satisfied: M$^1$ comprises a monovalent metal and M$^2$ comprises a trivalent element; M$^1$ is Li$^+$; and M$^2$ is B$^{3+}$.

2. The porous crystalline material of claim 1 wherein M$^1$ comprises a monovalent metal and M$^2$ comprises a trivalent element.

3. The porous crystalline material of claim 1 wherein M$^1$ is a monovalent metal cation selected from Li$^+$, Na$^+$, K$^+$, Cs$^+$, Rb$^+$, Cu$^+$, Ag$^+$, or Au$^+$.

4. The porous crystalline material of claim 1 wherein M$^1$ is a monovalent metal cation selected from Li$^+$, Cu$^+$, or Ag$^+$.

5. The porous crystalline material of claim 1 wherein M$^1$ is Li$^+$.

6. The porous crystalline material of claim 1 wherein M$^2$ is a trivalent element cation selected from B$^{3+}$, Al$^{3+}$, Ga$^{3+}$, In$^{3+}$, Fe$^{3+}$, Cr$^{3+}$, Sc$^{3+}$, Y$^{3+}$, or La$^{3+}$ wherein La is any lanthanide metal.

7. The porous crystalline material of claim 1 wherein M$^2$ is a trivalent element cation selected from B$^{3+}$, Al$^{3+}$, or Ga$^{3+}$.

8. The porous crystalline material of claim 1 wherein M$^2$ is B$^{3+}$.

9. The porous crystalline material of claim 1 wherein the tetrahedral framework has a framework type selected from the group consisting of crb, dft, cag, sod, mer, rho, ana, lta, dia, zni, gme, lcs, frl, gis, poz and moz.

10. The porous crystalline material of claim 1 wherein IM is an unsubstituted imidazolate group.

11. A porous crystalline material having a tetrahedral framework comprising a structure selected from the group consisting of IV, V, VI, or any combination thereof:

(IV)

-continued (V)

(VI)

wherein $A^1, A^2, A^3, A^4, A^5, A^6$, and $A^7$ can be either C or N, wherein $R^5$-$R^8$ are present when $A^1$ to $A^4$ comprise C, wherein $R^1$, $R^4$ or $R^9$ comprise a non-sterically hindering group that does not interfere with the adjacent $M^1$ or $M^2$, wherein $R^2$, $R^3$, $R^5$, $R^6$, $R^7$, and $R^8$ are each individually hydrogen, alkyl, halo, cyano, or nitro, wherein $M^1$ comprises a monovalent metal cation, wherein $M^2$ comprises a trivalent element cation, and wherein $R^{10}$, $R^{11}$, and $R^{12}$ are each individually electron withdrawing groups.

12. The porous crystalline material of claim 11 wherein $M^1$ is a monovalent metal cation selected from $Li^+$, $Na^+$, $K^+$, $Cs^+$, $Rb^+$, $Cu^+$, $Ag^+$, or $Au^+$.

13. The porous crystalline material of claim 11 wherein $M^1$ is a monovalent metal cation selected from $Li^+$, $Cu^+$, or $Ag^+$.

14. The porous crystalline material of claim 11 wherein $M^1$ is $Li^+$.

15. The porous crystalline material of claim 11 wherein $M^2$ is a trivalent element cation selected from $B^{3+}$, $Al^{3+}$, $Ga^{3+}$, $In^{3+}$, $Fe^{3+}$, $Cr^{3+}$, $Sc^{3+}$, $Y^{3+}$, or $La^{3+}$ wherein La is any lanthanide metal.

16. The porous crystalline material of claim 11 wherein $M^2$ is a trivalent element cation selected from $B^{3+}$, $Al^{3+}$, or $Ga^{3+}$.

17. The porous crystalline material of claim 11 wherein $M^2$ is $B^{3+}$.

18. The porous crystalline material of claim 11 wherein the tetrahedral framework has a framework type selected from the group consisting of crb, dft, cag, sod, mer, rho, ana, lta, dia, zni, gme, lcs, frl, gis, poz and moz.

19. The porous crystalline material of claim 11 and comprising a structure selected from the group consisting of VII, VIII, IX, X, XI, XII, XIII, XIV, XV, XVI, XVII, and XVIII:

(VII)

(VIII)

(IX)

(X)

(XI)

(XII)

(XIII)

(XIV)

(XV)

(XVI)

(XVII)

-continued (XVIII)

20. The porous crystalline material of claim 19 having structure VII wherein $M^1$ is $Li^+$, $M^2$ is $B^{3+}$, the tetrahedral framework has the cag framework type, and the as-synthesized material contains guest species within the tetrahedral framework.

21. A method of adsorbing a gas comprising contacting the gas with the porous crystalline material of claim 1.

22. The method of claim 21 wherein the gas is hydrogen, nitrogen, oxygen, a noble gas, carbon monoxide, carbon dioxide, a hydrocarbon or an amine.

23. A method of separating a gas from a fluid stream containing the gas comprising contacting the fluid stream with the porous crystalline material of claim 1.

24. The method of claim 23 wherein the gas is hydrogen, nitrogen, oxygen, a noble gas, carbon monoxide, carbon dioxide, a hydrocarbon or an amine.

25. A method of adsorbing a gas comprising contacting the gas with the porous crystalline material of claim 11.

26. The method of claim 21 wherein the gas is hydrogen, nitrogen, oxygen, a noble gas, carbon monoxide, carbon dioxide, a hydrocarbon or an amine.

27. A method of separating a gas from a fluid stream containing the gas comprising contacting the fluid stream with the porous crystalline material of claim 11.

28. The method of claim 24 wherein the gas is hydrogen, nitrogen, oxygen, a noble gas, carbon monoxide, carbon dioxide, a hydrocarbon or an amine.

* * * * *